(12) United States Patent
Gakh et al.

(10) Patent No.: US 8,242,284 B1
(45) Date of Patent: Aug. 14, 2012

(54) ANTI-CANCER AGENTS BASED ON 6-TRIFLUOROMETHOXYBENZIMIDAZOLE DERIVATIVES AND METHOD OF MAKING

(75) Inventors: Andrei A. Gakh, Bethesda, MD (US); Mykhaylo V. Vovk, Kyiv (UA); Nina V. Mel'nychenko, Kyiv (UA); Volodymyr A. Sukach, Brovary (UA)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 12/862,168

(22) Filed: Aug. 24, 2010

Related U.S. Application Data

(60) Provisional application No. 61/244,128, filed on Sep. 21, 2009.

(51) Int. Cl.
 *C07D 235/18* (2006.01)
(52) U.S. Cl. .................................................. 548/306.4
(58) Field of Classification Search ............... 548/306.4
 See application file for complete search history.

(56) References Cited

U.S. PATENT DOCUMENTS

| 5,656,649 | A  | * | 8/1997  | Lunkenheimer et al. | ..... 514/394 |
| 6,303,645 | B1 | * | 10/2001 | Sircar et al. | .................. 514/394 |
| 6,576,631 | B1 | * | 6/2003  | Shibata et al. | ................ 514/241 |

FOREIGN PATENT DOCUMENTS

WO   WO2008059026   *   5/2008

OTHER PUBLICATIONS

Banker and Rhodes, Modern Pharmaceutics, 2007, Marcel Dekker, Inc, 3rd Edition, p. 596.*
'Metabolite', http://www.encyclopedia.com/doc/1E1-metabolit. html, accessed Jan. 25, 2008.*
Shishido et al, Synthesis of benzamide derivatives as TRPV1 antagonists, 2008, Bioorganic and Medicinal Chemistry Letters, vol. 18, p. 1072-1078.*

* cited by examiner

*Primary Examiner* — Noble Jarrell
*Assistant Examiner* — Karen Cheng
(74) *Attorney, Agent, or Firm* — Mark C. Lang; Bradley W. Smith; John T. Lucas

(57) ABSTRACT

The present disclosure relates to novel compounds having the structural Formulas (1a,1b), stereoisomers, tautomers, racemics, prodrugs, metabolites thereof, or pharmaceutically acceptable salt and/or solvate thereof as chemotherapy agents for treating of cancer, particularly androgen-independent prostate cancer. The disclosure also relates to methods for preparing said compounds, and to pharmaceutical compositions comprising said compounds.

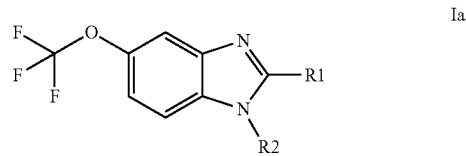

Ia

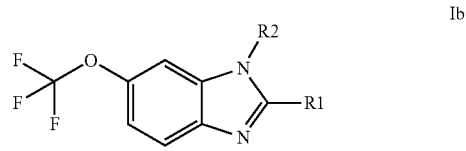

Ib

1 Claim, No Drawings

ANTI-CANCER AGENTS BASED ON 6-TRIFLUOROMETHOXYBENZIMIDAZOLE DERIVATIVES AND METHOD OF MAKING

CROSS-REFERENCE TO RELATED APPLICATION

The present patent application claims the benefit of the earlier priority filing date of U.S. Provisional Patent Application, Ser. No. 61/244,128, filed on Sep. 21, 2009, and entitled "Novel Anti-Cancer Agents Based on 6-Trifluoromethoxybenzimidazole Derivatives," the contents of which are incorporated in full by reference herein.

CONTRACTUAL ORIGIN OF THE INVENTION

This invention was made with United States Government support under a U.S. Department of Energy contract. The U.S. Government has certain rights in the present invention pursuant to Contract No. #200c between the Department of Energy (DOE), Science and Technology Center in Ukraine (STCU) and the Institute of Organic Chemistry of National Academy of Sciences of Ukraine, dated Jul. 1, 2008.

FIELD OF THE INVENTION

The present invention relates to novel anti-cancer agents based on 6-trifluoromethoxybenzimidazole derivatives that can be used in prostate cancer therapy. The present invention also relates to methods of preparing said compounds, and to pharmaceutical compositions comprising said compounds. This invention describes a method for treating androgen-independent prostate cancer using 6-trifluoromethoxybenzimidazole derivatives as chemotherapy agents.

BACKGROUND OF THE INVENTION

Prostate cancer is one of the most common forms of cancer, and the second leading cause of cancer deaths among men in the U.S. In 2005, 185,895 new cases of prostate cancer were diagnosed in the United States, and 28,905 men died of the cancer. The incidence of prostate cancer in the United States significantly decreased in the early 1990s but has remained level since 1995.

Current treatment options include localized therapy, such as surgery and/or radiotherapy for early diagnosed patients. Unfortunately, more than 30% of patients will eventually develop metastatic disease. Treatment for metastatic forms of prostate cancer typically involves hormone level manipulation procedures and/or radiotherapy, but rarely results in improving odds of long-term survival. The use of "classic" anti-proliferative agents such as Docetaxel® for the chemotherapy of androgen-independent stages of prostate cancer results only in marginal improvement of life expectancy. There are several promising new compounds aimed at chemotherapy of hormone-refractory prostate cancer, such as Abiraterone®. However, it is too early to tell whether Abiraterone® chemotherapy will have long term survival benefits. As a result, there is a strong need for new compound classes that can be used for hormone-refractory prostate cancer chemotherapy.

There are several patents describing the use of substituted benzimidazoles for cancer chemotherapy. However, none of these patents are directly related to the use of 6-trifluoromethoxybenzimidazole derivatives for the treatment of cancer, specifically chemotherapy of prostate cancer.

BRIEF SUMMARY OF THE INVENTION

The present invention relates to novel compounds having the structural Formulas (1a, 1b), stereoisomers, tautomers, racemics, prodrugs, metabolites thereof, or pharmaceutically acceptable salt and/or solvate thereof,

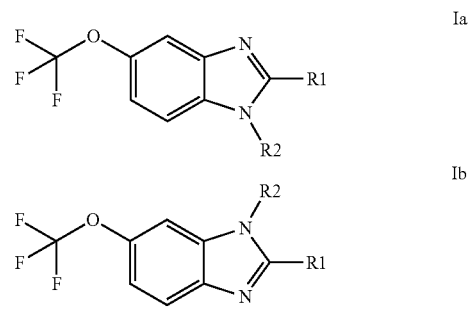

Wherein:

R1 is $C_{1-8}$ alkyl, phenyl, benzyl or a 5-or 6-membered ring heterocycle containing 1, 2 or 3 heteroatoms each independently selected from O, N and S and additionally having 0 or 1 oxo groups and 0 or 1 fused benzo rings, wherein the $C_{1-8}$ alkyl, phenyl, benzyl or heterocycle is substituted by 1, 2 or 3 substituents selected from —OR, —SR$^a$, —NR$^a$R$^a$, —CO$_2$R$^a$, —OC(=O)R$^a$, —C(=O)NA$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and $C_{1-3}$ haloalkyl; and wherein the phenyl, benzyl or heterocycle is additionally substituted by 0, 1 or 2 substituents selected from $C_{1-6}$ alkyl, phenyl or benzyl;

R2 is H, $C_{1-6}$ alkyl, —(CH$_2$)$_m$ phenyl, —(CH$_2$)$_m$ naphthyl or —(CH$_2$)$_m$ heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings, wherein the $C_{1-6}$ alkyl, —(CH$_2$)$_m$ phenyl, —(CH$_2$)$_m$ naphthyl or —(CH$_2$)$_m$ heterocycle are substituted with 0, 1 or 2 substituents selected from —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and $C_{1-3}$ haloalkyl;

R$^a$ is H, $C_{1-6}$ alkyl, $C_{1-3}$ haloalkyl, phenyl or benzyl; m is 0, 1, 2 or 3.

The compounds of the present invention have been prepared and demonstrated inhibition of DU-145 cell proliferation in dose-response.

The invention also relates to methods for preparing said compounds, to pharmaceutical compositions comprising said compounds, and to use of said compounds in methods for treatment of the human body.

DETAILED DESCRIPTION OF THE INVENTION

The present invention is a result of our ongoing efforts to find novel fluoroheterocyclic antiproliferative agents as potential treatments for androgen-independent prostate cancer.

The compounds of the invention are the selective ligands—derivatives of the structure (Formula (1a, 1b)), which are 6-trifluoromethoxybenzimidazole derivatives.

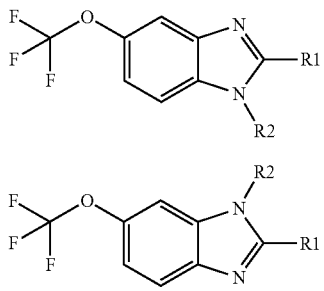

Wherein:

R1 is $C_{1-8}$ alkyl, phenyl, benzyl or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$ alkyl, phenyl, benzyl or heterocycle is substituted by 1, 2 or 3 substituents selected from —OR, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$ haloalkyl; and wherein the phenyl, benzyl or heterocycle is additionally substituted by 0, 1 or 2 substituents selected from $C_{1-6}$ alkyl, phenyl or benzyl;

R2 is H, $C_{1-6}$ alkyl, —$(CH_2)_m$ phenyl, —$(CH_2)_m$ naphthyl or —$(CH_2)_m$ heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings, wherein the $C_{1-6}$ alkyl, —$(CH_2)_m$ phenyl, —$(CH_2)_m$ naphthyl or —$(CH_2)_m$ heterocycle are substituted with 0, 1 or 2 substituents selected from —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$ haloalkyl; and $R^a$ is H, $C_{1-6}$ alkyl, $C_{1-3}$ haloalkyl, phenyl or benzyl; m is 0, 1, 2 or 3.

Another aspect of the invention is a pharmaceutical composition comprising a therapeutically-effective amount of a compound according to any of the above embodiments and a pharmaceutically acceptable diluent or carrier.

$C_{y-z}$ alkyl, unless otherwise specified, means an alkyl chain containing a minimum Y total carbon atoms and a maximum Z total carbon atoms.

The term "oxo" means a double bonded oxygen (=O).

The compounds of the invention may contain heterocyclic substituents that are 5- or 6 membered ring heterocycles containing 1, 2 or 3 heteroatoms each independently selected from O, N and S, and additionally having 0 or 1 oxo groups, and 0 or 1 fused benzo rings. A nonexclusive list containing specific examples of such heterocycles are as follows:

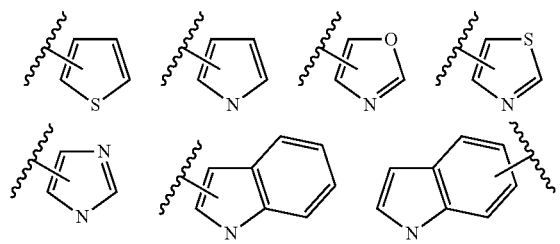

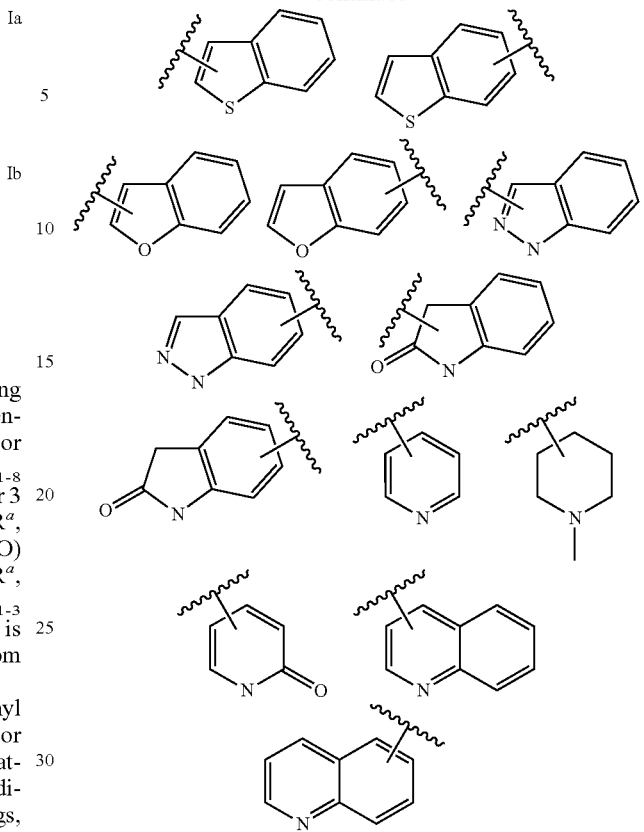

wherein the crossed bond represents that the heterocycle may be attached at any available position on either the heterocycle or the benzo ring.

Some of the compounds of the present invention are capable of forming salts with various inorganic and organic acids and bases, and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts, such as aluminum, calcium and magnesium salts, salts with organic bases, such as dicyclohexylamine salts, N-methyl-D-glucamine, and salts with amino acids, such as arginine, lysine, ornithine, and so forth. Also, basic nitrogen containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product. The salts may be formed by conventional means, such as by reacting the free base form of the product with one or more equivalents of the appropriate acid in a solvent or medium in which the salt is insoluble, or in a solvent, such as water, which is removed in vacuo or by freeze drying or by exchanging the anions of an existing salt for another anion on a suitable ion-exchange resin.

Compounds of the present invention are shown to have high selectivity for prostate cancer cells in vitro. Thus, these compounds, and compositions containing them, may be used as therapeutic agents in the treatment of various cancer diseases, such as prostate cancer.

The present invention also provides compositions including an effective amount of compounds of the present invention, including the nontoxic addition salts, amides and esters thereof, which may serve to provide the above-recited therapeutic benefits. Such compositions may also be provided together with physiologically-tolerable liquid, gel or solid diluents, adjuvants and excipients. The compounds of the present invention may also be combined with other compounds known to be used as therapeutic agents for the above or other indications.

These compounds and compositions may be administered by qualified health care professionals to humans in a manner similar to other therapeutic agents. The preparation may also be emulsified. The active ingredient is often mixed with diluents which are physiologically tolerable and compatible with the active ingredient. Suitable diluents are, for example, water, saline, dextrose, glycerol, or the like, and combinations thereof. In addition, if desired, the compositions may contain minor amounts of auxiliary substances, such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders may include, for example, polyalkylene glycols or triglycerides; such suppositories may be formed from mixtures containing the active ingredient. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders.

Synthesis

Compounds within the scope of the present invention may be synthesized chemically by means well known in the art. The following examples are meant to show general synthetic schemes, which may be used to produce many different variations by employing various commercially-available starting materials. These examples are meant only as guides on how to make some compounds within the scope of the invention, and should not be interpreted as limiting the scope of the invention.

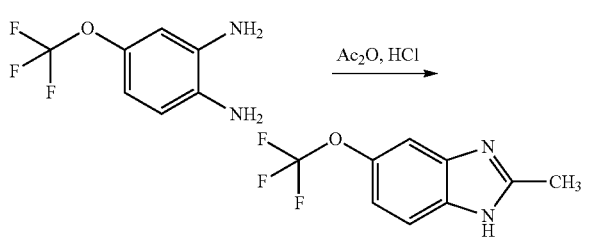

2-Methyl-5-trifluoromethoxybenzimidazole. The starting material, 2-amino-4-trifluoromethoxyaniline, was obtained by the method of Yagupolskii, L. M. et al. (Yagupolskii L. M., Troitskaya V. I. J. Gen. Chem. USSR Engl. Transl., 1961, Vol. 31, p. 845; Chem. Abstr. 1961, Vol. 55, p. 22830f). The procedure of Philips, M. A. (Philips M. A. J. Chem. Soc. 1929, p. 2820-2828) was used to produce 2-methyl-5-trifluoromethoxybenzimidazole. To 2-amino-4-trifluoromethoxyaniline (0.7 g, 0.0036 Mol) acetic acid anhydride (1.5g, 0.0146 Mol) was carefully added at 20° C. and the mixture was stirred 5 minutes at this temperature. Then 2-3 drops of concentrated aqueous HCl was added with stirring, and the mixture was refluxed for 7 hours The reaction solution was cooled and diluted with water (10 mL), 0.5 g of charcoal was added, and the mixture was refluxed more 5-10 min. After cooling, the mixture was filtered and resulted clear filtrate was washed with ether (2×10 mL). The water layer was neutralized with excess of dilute $NH_4OH$ -(charcoal was filtered) The precipitate was filtered, washed with water and dried to give a solid (0.34 g, 44% by wt. pure). M.p. 135-137° C. $^1H$ NMR (DMSO-$d_6$): 2.49 (s, 3H), 7.17 (d, J=8.5 Hz, 1H), 7.34 (s, 1H), 7.62 (d, J=8.5 Hz, 1H). $^{13}C$ NMR (DMSO-$d_6$): 14.47, 107.44, 114.19, 117.25, 120.28 (q, J=255.2 Hz), 137.06, 139.46, 143.09, 153.26. $^{19}F$ NMR (DMSO-$d_6$): —57.41. $[M+1]^+$ 217.

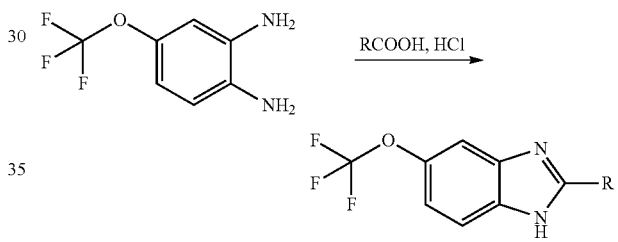

2-Hydroxymethyl- and 2-ethyl-5-trifluoromethoxybenzimidazole. The procedure of Philips, M. A. was used. A mixture of 2-amino-4-trifluoromethoxyaniline (0.7 g, 0.0036 Mol) and corresponding carboxylic acid (0.00546 Mol) in HCl (3.5 ml, 4N) was refluxed for 6 h. Water (5 mL), and 0.5 g of charcoal were added, and the mixture was refluxed 10-15 min. After cooling, the mixture was filtered and resulted clear filtrate was washed with ether (2×10 mL). The water layer was neutralized with excess of diluted $NH_4OH$, the precipitate was filtered, washed with water, and dried.

2-Hydroxymethyl-5-trifluoromethoxybenzimidazole. Glycolic acid was used, R=(HO)$CH_2$. Yield 0.65 g (75 wt. %). M.p. 192-194° C. $^1H$ NMR (DMSO-$d_6$): 4.68 (d, 5.5 Hz, 2H), 5.67 (t, 5.5 Hz, 2H), 7.05 (d, J=8.0 Hz, 1H), 7.38 (s, 1H), 7.49 (br s, 1H), 12.48 (br s, 1H). $^{13}C$ NMR (DMSO-$d_6$): 57.62, 104.44, 110.79, 111.98, 114.70, 118.20, 120.08 (q, J=254.8 Hz), 143.21, 157.22. $^{19}F$ NMR (DMSO-$d_6$): –57.76. $[M+1]^+$ 233.

2-Ethyl-5-trifluoromethoxybenzimidazole. Propionic acid was used, R=$CH_3CH_2$. Yield 0.66 g (78 wt. %). M.p. 135-137° C. $^1H$ NMR (DMSO-$d_6$): 1.34 (t, J=3H), 2.82 (q, J=2H), 7.02 (m, 1H), 7.36 (m, 2H), 12.33 (br s, 1H). $^{13}C$ NMR (DMSO-$d_6$): 11.93, 21.93, 103.75, 112.02, 110.53, 114.55, 118.45, 120.30 (q, J=255.0 Hz), 143.05, 158.14. $^{19}F$ NMR (DMSO-$d_6$): –57.47. $[M+1]^+$ 231.

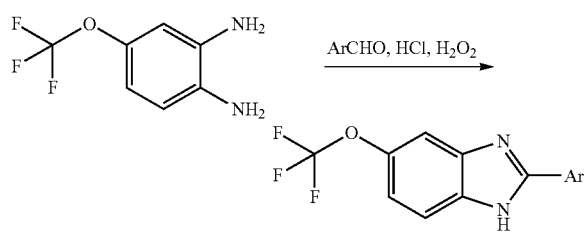

2-Aryl-5-trifluoromethoxybenzimidazole. The modified procedure of Bahrami, K. et. al. (Bahrami K., Khodaei M. M., Kavianinia I. Synthesis 2007, p. 547-550) was used. A solution of 2-amino-4-trifluoromethoxyaniline (0.7 g, 0.0036 Mol) in acetonitrile —$CH_3CN$ (5 mL) was mixed with aldehyde (0.0037 Mol) in $CH_3CN$ (5 mL) at 20° C. and stirred for 5-10 min. Aqueous 30% $H_2O_2$ (0.025 Mol) and concentrated 35% aqueous HCl (0.0126 Mol) were added at 20° C. and the mixture was stirred at this temperature for the 2-5 h (the progress of the reaction was monitored by TLC). Precipitate formed was filtered, washed with $CH_3CN$ (2×10 mL) and dried.

2-Phenyl-5-trifluoromethoxybenzimidazole. Benzaldehyde was used, Ar=$C_6H_5$. Yield 0.76 g (71 wt. %). M.p. 208-210° C. $^1$H NMR (DMSO-$d_6$): 7.31 (d, J=8.5 Hz, 1H), 7.38 (m, 2H), 7.49 (t, J=8.5 Hz, 1H), 7.83 (s, 1H), 7.95 (d, J=8.5 Hz, 1H), 8.57 (d, J=7.0 Hz, 2H). $^{13}$C NMR (DMSO-$d_6$): 107.87, 115.26, 116.42, 120.21 (q, J=255.1 Hz), 126.90, 127.98, 128.84, 130.73, 135.91, 138.10, 144.17, 152.51. $^{19}$F NMR (DMSO-$d_6$): −57.60. [M+1]$^+$ 279.

2-(4-Methylphenyl)-5-trifluoromethoxybenzimidazole. 4-Methylbenzaldehyde was used, Ar=4-$CH_3C_6H_4$ Yield 0.55 g (51 wt. %). M.p. 203-205° C. $^1$H NMR (DMSO-$d_6$): 2.37 (s, 3H), 7.18 (d, J=8.5 Hz, 1H), 7.36 (d, J=8.0 Hz, 2H), 7.64 (m, 2H), 8.08 (d, J=8.0 Hz, 2H), 13.12 (br s, 1H). $^{13}$C NMR (DMSO-$d_6$): 20.90, 115.75, 120.00 (q, J=255.6 Hz), 126.55, 126.93, 129.51, 140.05, 143.62, 153.56. $^{19}$F NMR (DMSO-$d_6$): −57.29. [M+1]$^+$ 293.

2-(4-Isopropylphenyl)-5-trifluoromethoxybenzimidazole. 4-Isopropylbenzaldehyde was used, Ar=4-$(CH_3)_2CHC_6H_4$ Yield 0.3 g (25 wt. %). M.p. 203-205° C. $^1$H NMR (DMSO-$d_6$): 1.27 (d, J=6.9 Hz, 6H), 3.03 (m, 1H), 7.52 (d, J=8.4 Hz, 1H), 7.60 (d, J=8.1 Hz, 2H), 7.80 (s, 1H), 7.92 (d, J=8.4 Hz, 1H), 8.33 (d, J=8.1 Hz, 2H). $^{13}$C NMR (DMSO-$d_6$): 23.33, 33.54, 107.09, 115.48, 119.01, 120.02 (q, J=255.5 Hz), 121.23, 127.55, 128.23, 131.58, 133.16, 145.38, 151.00, 154.34. $^{19}$F NMR (DMSO-$d_6$): −57.02. [M+1]$^+$ 321.

2-(4-Fluorophenyl)-5-trifluoromethoxybenzimidazole. 4-Fluorobenzaldehyde was used, Ar=4-$FC_6H_4$ Yield 0.55 g (51 wt. %). M.p. 158-160° C. $^1$H NMR (DMSO-$d_6$): 7.17 (d, J=8.5 Hz, 1H), 7.41 (t, J=8.0 Hz, 2H), 7.64 (m, 2H), 8.21 (t, J=8.0 Hz, 2H), 13.17 (br s, 1H). $^{13}$C NMR (DMSO-$d_6$): 104.45, 111.49, 112.15, 115.31, 115.95, 120.07 (q, J=255.5 Hz), 126.25, 128.90, 143.69, 152.55, 162.29, 164.26. $^{19}$F NMR (DMSO-$d_6$): −57.71 (s, 3F), −110.65 (s, 1F). [M+1]$^+$ 297.

2-(4-Chlorophenyl)-5-trifluoromethoxybenzimidazole. 4-Chlorobenzaldehyde was used, Ar=4-$ClC_6H_4$ Yield 0.61 g (53 wt. %). M.p. 190-192° C. $^1$H NMR (DMSO-$d_6$): 7.37 (d, J=9.0 Hz, 1H), 7.71 (m, 3H), 7.81 (d, J=9.0 Hz, 1H), 8.29 (d, J=8.4 Hz, 2H). $^{13}$C NMR (DMSO-$d_6$): 107.48, 115.61, 118.36, 120.25 (q, J=255.4 Hz), 124.19, 129.39, 129.46, 133.16, 134.96, 137.23, 145.08, 150.49. $^{19}$F NMR (DMSO-$d_6$): −58.04. [M+1]$^+$ 313.6.

2-(4-Methoxyphenyl)-5-trifluoromethoxybenzimidazole. 4-Methoxybenzaldehyde was used, Ar=4-$CH_3OC_6H_4$ Yield 0.46 g (40 wt. %). M.p. 200-202° C. $^1$H NMR (DMSO-$d_6$): 3.88 (s, 3H), 7.22 (d, J=8.7 Hz, 2H), 7.36 (d, J=9.0 Hz, 1H), 7.66 (s, 1H), 7.78 (d, J=9.0 Hz, 1H), 8.23 (d, J=8.7 Hz, 2H). $^{13}$C NMR (DMSO-$d_6$): 55.74, 107.71, 114.96, 115.22, 117.37, 118.38, 120.39 (q, J=255.3 Hz), 129.36, 134.48, 136.58, 144.62, 152.36, 162.30. $^{19}$F NMR (DMSO-$d_6$): −57.42. [M+1]$^+$ 309.

2-(4-Hydroxy-3-methoxyphenyl)-5-trifluoromethoxybenzimidazole. 4-Hydroxy-3-methoxybenzaldehyde was used, Ar=4-HO-3-$CH_3OC_6H_3$ Yield 0.42 g (36 wt. %). M.p. 188-190° C. $^1$H NMR (DMSO-$d_6$): 3.94 (s, 3H), 7.07 (d, J=8.4 Hz, 2H), 7.48 (d, J=9.0 Hz, 1H), 7.75 (s, 1H), 7.85 (m, 3H), 8.05 (s, 1H), 10.43 (br s, 1H). $^{13}$C NMR (DMSO-$d_6$): 56.23, 106.73, 111.98, 113.59, 115.02, 116.20, 118.88, 120.35 (q, J=255.5 Hz), 122.34, 131.10, 132.64, 145.33, 148.28, 151.31, 152.02. $^{19}$F NMR (DMSO-$d_6$): −57.44. [M+1]$^+$ 325.

2-(4-Methoxy-3-benzyloxyphenyl)-5-trifluoromethoxybenzimidazole. 4-Methoxy-3-benzyloxybenzaldehyde was used, Ar=4-$CH_3O$-3-$C_6H_5CH_2OC_6H_3$ Yield 0.63 g (40 wt. %). M.p. 226-228° C. $^1$H NMR (DMSO-$d_6$): 3.88 (s, 1H), 5.23 (s, 2H), 7.43 (m, 8H), 7.65 (s, 1H), 7.73 (d, J=9.0 Hz, 1H), 7.87 (d, J=8.4 Hz, 1H), 8.05 (s, 1H). $^{13}$C NMR (DMSO-$d_6$): 55.87, 70.28, 107.42, 112.17, 112.36, 115.02, 117.37, 118.19, 119.19, 120.30 (q, J=255.4), 121.33, 127.99, 133.94, 135.97, 136.53, 138.53, 144.55, 148.06, 152.08, 152.33. $^{19}$F NMR (DMSO-$d_6$): −57.42. [M+1]$^+$ 415.

2-(5-Bromo-2-methoxyphenyl)-5-trifluoromethoxybenzimidazole. 5-Bromo-2-methoxybenzaldehyde was used, Ar=5-Br-2-$CH_3OC_6H_3$ Yield 0.7 g (50 wt. %). M.p. 175-178° C. $^1$H NMR (DMSO-$d_6$): 4.07 (s, 3H), 7.33 (d, J=9.0 Hz, 1H), 7.47 (d, J=8.1 Hz, 1H), 7.84 (m, 2H), 7.92 (d, J=9.0 Hz, 1H), 8.51 (d, J=2.4 Hz, 1H). $^{13}$C NMR (DMSO-$d_6$): 56.79, 107.29, 112.40, 113.71, 115.24, 115.98, 119.16, 120.32 (q, J=255.6 Hz), 131.26, 132.19, 132.79, 137.10, 145.45, 146.72, 156.97. $^{19}$F NMR (DMSO-$d_6$): −57.44. [M+1]$^+$ 389.

2-(3-Methoxyphenyl)-5-trifluoromethoxybenzimidazole. 3-Methoxybenzaldehyde was used, Ar=3-$CH_3OC_6H_4$ Yield 0.45 g (40 wt. %). M.p. 192-194° C. $^1$H NMR (DMSO-$d_6$): 3.90 (s, 3H), 7.24 (d, J=8.4 Hz, 1H), 7.45 (d, 8.4 Hz, 1H), 7.59 (t, J=8.4 Hz, 1H), 7.76 (s, 1H), 7.92 (m, 3H). $^{13}$C NMR (DMSO-$d_6$): 55.68, 107.39, 112.70, 115.56, 118.49, 118.79, 119.96, 120.15 (q, J=256.5 Hz), 126.02, 130.62, 132.74, 134.51, 145.13, 151.25, 159.75. $^{19}$F NMR (DMSO-$d_6$): −57.41. [M+1]$^+$ 309.

2-(2,4-Dimethoxyphenyl)-5-trifluoromethoxybenzimidazole. 2,4-Dimethoxybenzaldehyde was used, Ar=2,4-$(CH_3O)_2C_6H_3$ Yield 0.61 g (50 wt. %). M.p. 201-203° C. $^1$H NMR (DMSO-$d_6$): 3.94 (s, 3H), 4.13 (s, 3H), 6.83 (m, 2H), 7.44 (d, 8.5 Hz, 1H), 7.81 (s, 1H), 7.95 (d, 8.8 Hz, 1H), 8.44 (d, 8.5 Hz, 1H). $^{13}$C NMR (DMSO-$d_6$): 55.88, 56.40, 98.72, 104.13, 106.81, 107.25, 115.28, 118.29, 120.02 (q, J=255.1 Hz), 131.13, 131.56, 132.71, 144.97, 148.30, 159.63, 164.82. $^{19}$F NMR (DMSO-$d_6$): −57.42. [M+1]$^+$ 339.

2-(1,3-Benzodioxol-5-yl)-5-trifluoromethoxybenzimidazole. 1,3-Benzodioxole-5-carbaldehyde was used, Ar=3,4-$(CH_2OCH_2)C_6H_3$ Yield 0.35 g (30 wt. %). M.p. 211-213° C. $^1$H NMR (DMSO-$d_6$): 6.19 (s, 2H), 7.21 (d, 8.1 Hz, 1H), 7.36 (d, 9.0 Hz, 1H), 7.67 (s, 1H), 7.82 (m, 3H). $^{13}$C NMR (DMSO-$d_6$): 102.29, 107.23, 109.11, 115.18, 117.98, 118.81, 120.17 (q, J=256.6 Hz), 123.26, 133.04, 134.89, 144.86, 148.17, 150.88, 151.39. $^{19}$F NMR (DMSO-$d_6$): −57.40. [M+1]$^+$ 323.

2-(4-Methylthiophenyl)-5-trifluoromethoxybenzimidazole. 4-Methylthiobenzaldehyde was used, Ar=4-$CH_3SC_6H_4$ Yield 0.42 g (35 wt. %). M.p. 200-202° C. $^1$H NMR (DMSO-$d_6$): 2.59 (s, 3H), 7.47 (d, J=9.0 Hz, 1H), 7.55 (d, J=8.6 Hz, 2H), 7.76 (s, 1H), 7.87 (d, J=9.0 Hz, 1H), 8.28 (d, J=8.6 Hz, 2H). $^{13}$C NMR (DMSO-d$_6$): 13.96, 106.93, 115.34, 118.89, 119.30, 120.06 (q, J=255.8), 125.65, 128.19, 131.57, 133.17, 145.35, 145.95, 150.63. $^{19}$F NMR (DMSO-d$_6$): −56.99. [M+1]$^+$ 325.

2-(4-Diethylaminophenyl)-5-trifluoromethoxybenzimidazole. 4-Diethylaminobenzaldehyde was used, Ar=4-(CH$_3$CH$_2$)$_2$NC$_6$H$_4$ Yield 0.7 g (55 wt. %). M.p. 168-173° C. $^1$H NMR (DMSO-d$_6$): 1.15 (t, J=6.9 Hz, 6H), 3.47 (q, J=6.9 Hz, 4H), 6.91 (d, J=8.6 Hz, 2H), 7.45 (d, J=9.0 Hz, 1H), 7.68 (s, 1H), 7.81 (d, J=9.0 Hz, 1H), 8.20 (d, J=8.6 Hz, 2H). $^{13}$C NMR (DMSO-d$_6$): 12.24, 44.00, 106.17, 107.13, 111.14, 114.40, 118.41, 120.01 (q, J=256.5), 129.97, 130.76, 132.26, 145.07, 151.07, 151.32. $^{19}$F NMR (DMSO-d$_6$): −57.51. [M+1]$^+$ 350.

2-(3-Nitrophenyl)-5-trifluoromethoxybenzimidazole. 3-Nitrobenzaldehyde was used, Ar=3-NO$_2$C$_6$H$_4$ Yield 0.5 g (42 wt. %). M.p. 193-195° C. $^1$H NMR (DMSO-d$_6$): 7.35 (d, J=9.0 Hz, 1H), 7.73 (s, 1H), 7.81 (d, J=9.0 Hz, 1H), 7.93 (t, J=8.4 Hz, 1H), 8.41 (d, J=8.4 Hz, 1H), 8.70 d, J=9.0 Hz, 1H), 9.09 (s, 1H). $^{13}$C NMR (DMSO-d$_6$): 108.12, 115.92, 117.87, 120.10 (q, J=255.6), 121.84, 125.57, 130.93, 133.26, 134.83, 136.85, 144.84, 148.2, 150.10. $^{19}$F NMR (DMSO-d$_6$): −57.38. [M+1]$^+$ 324.

2-(2-Thienyl)-5-trifluoromethoxybenzimidazole. Thiophene-2-carbaldehyde was used, Ar=2-thienyl Yield 0.64 g (63 wt. %). M.p. 163-165° C. $^1$H NMR (DMSO-d$_6$): 7.36 (m, 2H), 7.51 (s, 1H), 7.80 (d, J=8.7 Hz, 1H), 8.02 (d, J=4.8 Hz, 1H), 8.27 (d, J=4.8 Hz, 1H). $^{13}$C NMR (DMSO-d$_6$): 107.26, 115.23, 118.15, 120.02 (q, J=255.2 Hz), 127.31, 128.91, 132.00, 132.99, 133.16, 134.83, 144.97, 146.86. $^{19}$F NMR (DMSO-d$_6$): −57.16. [M+1]$^+$ 285.

2-(4-Difluoromethoxyphenyl)-5-trifluoromethoxybenzimidazole. 4-Difluoromethoxybenzaldehyde was used, Ar=4-CHF$_2$OC$_6$H$_4$ Yield 0.7 g (56 wt. %). M.p. 185-187° C. $^1$H NMR (DMSO-d$_6$): 7.49 (m, 4H), 7.76 (s, 1H), 7.87 (d, J=8.8 Hz, 1H), 8.41 (d, J=9.0 Hz, 2H). $^{13}$C NMR (DMSO-d$_6$): 107.31, 115.54, 115.89 (t, J=257.6 Hz), 118.71, 118.91, 120.03 (q, J=255.4 Hz), 130.12, 132.40, 134.11, 138.54, 145.27, 150.46, 154.16. $^{19}$F NMR (DMSO-d$_6$): −57.43 (3F), −83.53 (1F), −83.92 (1F). [M+1]$^+$ 345.

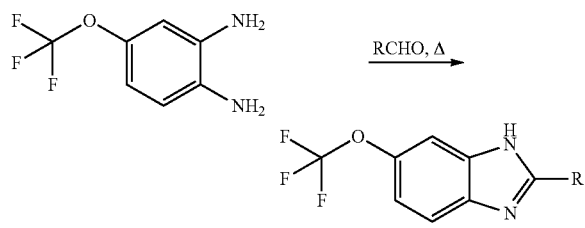

R = 2-furyl, 3-pyridyl 2-(2-Furyl)- and 2-(3-pyridyl)-6-trifluoromethoxybenzimidazole. The procedure of Jerchel, D. et. al. (Jerchel D., Fischer H., Kracht M. Ann Chem. 1952, Vol. 575, p. 162-173) was used. To stirred 2-amino-4-trifluoromethoxyaniline (0.7 g, 0.0036 Mol) the corresponding aldehyde (0.00364 Mol) was added dropwise at 20° C. and the mixture was stirred 0.5 h at this temperature. Water formed in the reaction was removed by azeotropic distillation with benzene under reduced pressure. Then nitrobenzene (5-7 mL) was added and the mixture was heated gradually for 30 min to reflux and refluxed more 2-3 h. After cooling to room temperature, the precipitate was filtered, washed with diethyl ether (2×10 mL) and dried.

2-(2-Furyl)-6-trifluoromethoxybenzimidazole. Furane-2-carbaldehyde was used, R=2-furyl. Yield 0.5 g (39.5 wt. %). M.p. 165-167° C. $^1$H NMR (DMSO-d$_6$): 6.75 (s, 1H), 7.23 (m, 2H), 7.60 (m, 2H), 7.98 (s, 1H), 13.22 (br s, 1H). $^{13}$C NMR (DMSO-d$_6$): 111.27, 112.40, 119.32, 120.15 (q, J=255.8 Hz), 143.78, 145.04, 145.61. $^{19}$F NMR (DMSO-d$_6$): −57.89. [M+1]$^+$ 269.

2-(3-Pyridyl)-6-trifluoromethoxybenzimidazole. Pyridine-3-carbaldehyde was used, R=3-pyridyl. Yield 0.69 g (68.5 wt. %). M.p. 197-199° C. $^1$H NMR (DMSO-d$_6$): 7.16 (d, J=7.5 Hz, 1H), 7.55 (br s, 2H), 7.66 (br s, 1H), 8.46 (d, J=7.5 Hz, 1H), 8.65 (s, 1H), 9.31 (s, 1H), 13.28 (s, 1H). $^{13}$C NMR (DMSO-d$_6$): 115.85, 120.31 (q, J=255.4 Hz), 123.62, 125.65, 133.68, 143.87, 147.52, 150.44, 150.76. $^{19}$F NMR (DMSO-d$_6$): −57.48. [M+1]$^+$ 280.

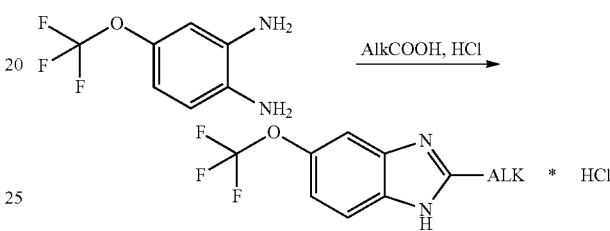

2-Alkyl-5-trifluoromethoxybenzimidazole hydrochloride. The modified procedure of Bahrami, K. et. al. was used. A mixture of 2-amino-4-trifluoromethoxyaniline (0.77 g, 0.004 Mol) and corresponding carboxylic acid (0.006 Mol) in HCl (10 ml, 4N) was refluxed for 10 h. The white precipitate formed was filtered, washed with 4N HCl and dried.

2-Benzyl-5-trifluoromethoxybenzimidazole hydrochloride. Phenylacetic acid was used, Alk=C$_6$H$_5$CH$_2$. Yield 1.07 g (82 wt. %). M.p. 177-180° C. $^1$H NMR (DMSO-d$_6$): 4.53 (s, 2H), 7.33 (t, J=7.0 Hz, 1H), 7.38 (m, 2H), 7.49 (m, 3H), 7.80 (s, 1H), 7.86 (d, J=8.8 Hz, 1H). $^{13}$C NMR (DMSO-d$_6$): 32.10, 107.11, 115.45, 118.97, 120.03 (q, J=257.6 Hz), 127.52, 128.80, 129.06, 130.25, 131.76, 133.87, 145.32, 154.64. $^{19}$F NMR (DMSO-d$_6$): −57.46. [M+1]$^+$ 293.

2-(2-Phenylethyl)-5-trifluoromethoxybenzimidazole hydrochloride. 2-Phenylpropionic acid was used, Alk=C$_6$H$_5$CH$_2$CH$_2$. Yield 0.71 g (52 wt. %). M.p. 195-197° C. $^1$H NMR (DMSO-d$_6$): 3.26 (t, J=7.2 Hz, 2H), 3.47 (t, J=7.2 Hz, 2H), 7.21 (m, 1H), 7.31 (m, 4H), 7.53 (d, J=7.8 Hz, 1H), 7.83 (s, 1H), 7.88 (d, J=8.7 Hz, 1H). $^{13}$C NMR (DMSO-d$_6$): 28.08, 31.92, 107.04, 115.32, 117.00, 119.07, 120.08 (q, J=253.9 Hz), 126.51, 128.14, 129.92, 131.36, 139.20, 145.37, 155.63. $^{19}$F NMR (DMSO-d$_6$): −57.49. [M+1]$^+$ 307.

2-(4-Methoxybenzyl)-5-trifluoromethoxybenzimidazole hydrochloride. (4-Methoxyphenyl)acetic acid was used, Alk=(4-CH$_3$OC$_6$H$_4$)CH$_2$. Yield 1.1 g (77 wt. %). M.p. 180-182° C. $^1$H NMR (DMSO-d$_6$): 3.74 (s, 3H), 4.46 (s, 2H), 6.94 (d, J=6.6 Hz, 2H), 7.43 (d, J=6.6 Hz, 2H), 7.49 (d, J=8.1 Hz, 1H), 7.80 (s, 1H), 7.86 (d, J=8.1 Hz, 1H). $^{13}$C NMR (DMSO-d$_6$): 31.27, 55.11, 107.19, 114.32, 115.50, 119.14, 120.05 (q, J=254.0 Hz), 125.57, 130.08, 130.40, 131.53, 145.39, 155.21, 158.78. $^{19}$F NMR (DMSO-d$_6$): −57.51. [M+1]$^+$ 323.

2-(4-Fluorobenzyl)-5-trifluoromethoxybenzimidazole hydrochloride. (4-Fluorophenyl)acetic acid was used, Alk=(4-FC$_6$H$_4$)CH$_2$. Yield 0.96 g (69 wt. %). M.p. 168-170° C. $^1$H NMR (DMSO-d$_6$): 4.53 (s, 2H), 7.21 (t, J=8.4 Hz, 2H), 7.54 (m, 3H), 7.79 (s, 1H), 7.87 (d, J=8.8 Hz, 1H). $^{13}$C NMR (DMSO-d$_6$): 31.37, 107.32, 115.53 (d, J=30.1 Hz), 115.60, 119.04, 120.04 (q, J=257.6 Hz), 130.19 (d, J=46.5 Hz), 131.30, 131.91, 145.33, 154.75, 160.67, 162.61. $^{19}$F NMR (DMSO-d$_6$): −57.52 (3F), −115.12 (1F). [M+1]$^+$ 311.

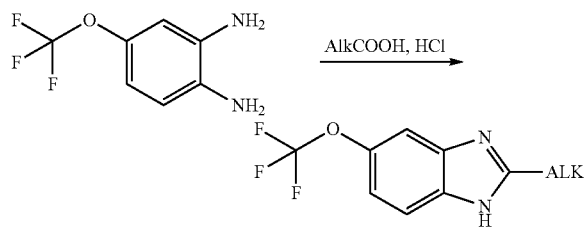

2-Alkyl-5-trifluoromethoxybenzimidazole. The modified procedure of Bahrami, K. et. al. was used. A mixture of 2-amino-4-trifluoromethoxyaniline (0.77 g, 0.004 Mol) and corresponding carboxylic acid (0.006 Mol) in HCl (10 ml, 4N) was refluxed for 10 h. The hot mixture was poured into ice-water potassium carbonate solution. The oil formed was crystallized after 12 hours, filtered, washed with water, dried, and crystallized from cyclohexane-isopropanole.

2-(5,6,7,8-Tetrahydronaphthalen-2-ylmethyl)-5-trifluoromethoxybenzimidazole. (5,6,7,8-Tetrahydronaphtalen-2-yl)acetic acid was used, Alk=5,6,7,8-tetrahydronaphtalen-2-yl. Yield 0.66 g (47 wt. %). M.p. 88-90° C. $^1$H NMR (CDCl$_3$): 1.72 (m, 4H), 2.51 (m, 2H), 2.66 (m, 2H), 4.13 (s, 2H), 6.87 (s, 1H), 6.94 (s, 2H), 7.10 (d, J=8.6 Hz, 1H), 7.32 (s, 1H), 7.41 (d, J=8.6 Hz, 1H), 10.40 (br s, 1H). $^{13}$C NMR (CDCl$_3$): 23.06, 29.07, 29.31, 35.50, 108.12, 115.08, 116.24, 120.02 (q, J=255.1 Hz), 126.11, 129.76, 132.86, 136.40, 137.05, 137.90, 138.88, 144.82, 156.29. $^{19}$F NMR (CDCl$_3$): −59.30. [M+1]$^+$ 347.

2-(Imidazo[2,1-b][1,3]thiazole-6-ylmethyl)-5-trifluoromethoxybenzimidazole. (Imidazo[2,1-b][1,3]thiazole-6-yl)acetic acid was used, Alk=imidazo[2,1-b][1,3]thiazole-6-yl. Yield 0.38 g (28 wt. %). M.p. 177-179° C. $^1$H NMR (CDCl$_3$): 4.35 (s, 2H), 6.81 (d, J=4.5 Hz, 1H), 7.04 (d, J=7.8 Hz, 1H), 7.39 (m, 4H), 8.91 (br s, 1H). $^{13}$C NMR (CDCl$_3$): 29.24, 108.33, 110.72, 112.51, 115.01, 116.09, 118.63, 122.85 (q, J=256.4 Hz), 136.89, 138.99, 142.83, 144.71, 149.97, 154.53. $^{19}$F NMR (CDCl$_3$): −59.35. [M+1]$^+$ 339.

5-Trifluoromethoxy-2-trifluoromethylbenzimidazole. Trifluoroacetic acid was used, Alk=CF$_3$. Yield 0.71 g (64 wt. %). M.p. 158-160° C. $^1$H NMR (DMSO-d$_6$): 7.42 (d, J=8.6 Hz, 1H), 7.77 (s, 1H), 7.84 (d, J=8.6 Hz, 1H). $^{13}$C NMR (DMSO-d$_6$): 118.66, 119.18 (q, J=270.2 Hz), 120.71 (q, J=255.2 Hz), 142.33 (q, J=38.9 Hz), 145.40. $^{19}$F NMR (DMSO-d$_6$): −57.41, −63.34. [M+1]$^+$ 271.

2-Phenoxymethyl-5-trifluoromethoxybenzimidazole. Phenoxyacetic acid was used, Alk=C$_6$H$_5$OCH$_2$. Yield 0.63 g (50 wt. %). M.p. 65-66° C. $^1$H NMR (DMSO-d$_6$): 5.35 (s, 2H), 6.96 (m, 1H), 7.10 (m, 2H), 7.22 (d, J=8.8 Hz, 1H), 7.32 (m, 2H), 7.56 (s, 1H), 7.68 (d, J=8.8 Hz, 1H). $^{13}$C NMR (DMSO-d$_6$): 64.13, 108.97, 115.27, 116.13, 120.02 (q, J=256.0 Hz), 121.77, 130.04, 137.54, 139.74, 144.07, 153.08, 158.54. $^{19}$F NMR (DMSO-d$_6$): −57.40. [M+1]$^+$ 309.

2-Propyl-5-trifluoromethoxybenzimidazole. Butyric acid was used, Alk=CH$_3$CH$_2$CH$_2$. Yield 0.42 g (42 wt. %). M.p. 88-90° C. $^1$H NMR (DMSO-d$_6$): 0.95 (t, J=7.5 Hz, 3H), 1.80 (q, J=7.5 Hz, 2H), 2.80 (t, J=7.5 Hz, 2H), 7.11 (d, J=8.0 Hz, 1H), 7.47 (m, 2H), 12.46 (br s, 1H). $^{13}$C NMR (DMSO-d$_6$): 14.07, 21.30. 30.97, 115.13, 120.01 (q, J=255.1 Hz), 143.59, 157.86. NMR (DMSO-d$_6$): −57.43. [M+1]$^+$ 245.

Cell Preparation: DU-145 cells (prostate carcinoma; catalog # HTB-81) were obtained from the ATCC and propagated in EMEM with Earles BSS supplemented with 10% FBS (fetal bovine serum), 2 mM L-glutamine, 100 U/mL penicillin, 100 µg/mL streptomycin, 1 mM sodium pyruvate, and 0.1 mM NEAA (Non-Essential Amino Acids). DU-145 cells were passaged in T-75 flasks prior to use in the assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were re-suspended at 1×10$^5$ cells per mL in tissue culture medium and added to the drug-containing microtiter plates in a volume of 100 µL.

Plate Format: Each plate contained cell control wells (cells only), experimental compound evaluation wells (cells plus compound only), and test compound colorimetric control wells (compound only). Samples were initially tested in triplicate for inhibition of DU-145 cell growth at 10 µM concentration for each compound with a single colorimetric control well. Secondary assay tested the compounds in triplicate using five half-logarithmic dilutions.

Tetrazolium Dye XTT Viability Endpoint: Following incubation at 37° C. in a 5% CO$_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT was metabolized by the mitochondrial enzymes of metabolically active cells to a soluble formazan product, allowing rapid quantitative analysis of the inhibition of DU-145 cell death by anti-prostate cancer test substances. XTT solution was prepared daily as a stock of 1 mg/mL in RPMI1640. Phenazine methosulfate (PMS) solution was prepared at 0.15 mg/mL in PBS (Phosphate—Buffered Saline) and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

IC$_{50}$ represents the concentration of a drug that is required for 50% inhibition in vitro. As shown in Table 1, the compositions at the beginning of the table are more effective inhibitors than those at the end of the table.

Results of Anti-proliferate Evaluation:

TABLE 1

| Compound | DU145 TC$_{50}$ (µM) |
|---|---|
| Tamoxifen Citrate | 20.0 |
| 2-methyl-5-trifluoromethoxybenzimidazole | >10.0 |
| 2-ethyl-5-trifluoromethoxybenzimidazole | >10.0 |
| 2-phenyl-5-trifluoromethoxybenzimidazole | 0.9 |

TABLE 1-continued

| Compound | DU145 TC$_{50}$ (μM) |
|---|---|
| (benzimidazole with OCF$_3$ and furan) | 1.8 |
| (benzimidazole with OCF$_3$ and pyridine) | 4.6 |

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A compound having the structural formula (1a) or (1b), a stereoisomer, tautomer, racemate or pharmaceutically acceptable salt thereof,

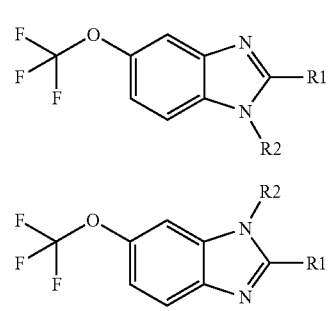

Wherein:
R1 is phenyl or benzyl, wherein the phenyl or benzyl is optionally substituted by 1, 2 or 3 substituents selected from —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$ haloalkyl; and wherein the phenyl or benzyl is additionally substituted by 0, 1 or 2 substituents selected from C$_{1-6}$ alkyl, phenyl or benzyl;
R2 is —(CH$_2$)$_m$ naphthyl; and
R$^a$ is H, C$_{1-6}$ alkyl, C$_{1-3}$ haloalkyl, phenyl or benzyl; m is 0, 1, 2 or 3.

* * * * *